(12) United States Patent
Casula

(10) Patent No.: US 8,270,254 B2
(45) Date of Patent: Sep. 18, 2012

(54) PHASED ARRAY ULTRASONIC CONTACT TRANSDUCER, WITH A FLEXIBLE WEDGE AND A PROFILOMETER

(75) Inventor: Olivier Casula, Longpont sur Orge (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 25 days.

(21) Appl. No.: 12/937,982

(22) PCT Filed: Apr. 21, 2009

(86) PCT No.: PCT/EP2009/054738
§ 371 (c)(1),
(2), (4) Date: Oct. 14, 2010

(87) PCT Pub. No.: WO2009/130216
PCT Pub. Date: Oct. 29, 2009

(65) Prior Publication Data
US 2011/0032800 A1    Feb. 10, 2011

(30) Foreign Application Priority Data
Apr. 23, 2008  (FR) ...................................... 08 52725

(51) Int. Cl.
*G01N 29/24*  (2006.01)
(52) U.S. Cl. ....................................................... 367/138
(58) Field of Classification Search .................. 367/138, 367/152; 310/323.01; 600/472
See application file for complete search history.

(56) References Cited

U.S. PATENT DOCUMENTS

| 4,526,168 A | 7/1985 | Hassler |
| 5,913,825 A | 6/1999 | Watanabe |
| 6,424,597 B1 | 7/2002 | Bolomey |
| 2007/0167800 A1 | 7/2007 | Casula |
| 2011/0032800 A1* | 2/2011 | Casula ........................ 367/138 |

FOREIGN PATENT DOCUMENTS

FR         2429429       1/1980

OTHER PUBLICATIONS

International Search Report, PCT/EP2009/054738, dated Jul. 27, 2009.
French Preliminary Search Report, FR 08 52725, dated Nov. 27, 2008.
International Preliminary Report on Patentability for International Application No. PCT/EP2009/054738, dated Feb. 17, 2011.

* cited by examiner

*Primary Examiner* — Daniel Pihulic
(74) *Attorney, Agent, or Firm* — Nixon Peabody LLP

(57) ABSTRACT

Phased array ultrasonic contact transducer, with a flexible wedge and a profilometer. This transducer applies to the non-destructive monitoring of an object and comprises: a set of elements that are rigidly integral with each other, at least part of the elements serving as ultrasound transmitters, a wedge whereof at least the front face is flexible to be applied against the surface of the object and the rear face of which is made integral with the set of elements, and a profilometer to measure surface variations and supply signals representative thereof to allow the transmitters to create a focused ultrasonic beam whereof the characteristics are controlled in relation to the object.

9 Claims, 4 Drawing Sheets

PHASED ARRAY ULTRASONIC CONTACT TRANSDUCER, WITH A FLEXIBLE WEDGE AND A PROFILOMETER

CROSS REFERENCE TO RELATED APPLICATIONS OR PRIORITY CLAIM

This application is a national phase of International Application No. PCT/EP2009/054738, entitled "PHASED ARRAY ULTRASONIC CONTACT TRANSDUCER, WITH A FLEXIBLE WEDGE AND A PROFILOMETER", which was filed on Apr. 21, 2009, and which claims priority of French Patent Application No. 08 52725 filed Apr. 23, 2008.

DESCRIPTION

1. Technical Field

The present invention concerns a phased array ultrasonic contact transducer.

This transducer can be used in the industrial field to perform non-destructive monitoring, in the medical field, and in any field requiring that the transducer be in contact with the surface of an object to be monitored and that it be flexible enough to fit the shape of that surface (the words "deformable," "soft," and "flexible" being synonymous in this description).

Examples of applications include, in the industrial field, monitoring welding seams, elbows, and tappings, and in the medical field, monitoring the heel bone as well as the skull.

2. Background of the Invention

Single element ultrasonic contact transducers are increasingly being replaced with phased array transducers in which the electrical excitation of the elements is steered using delay laws to focus the ultrasound energy on different points of an object to be monitored by spatial-temporal synchronization.

These operations are conducted using control systems that are capable of simultaneously controlling several hundreds of elements and delay laws.

These known techniques are relatively well suited to monitoring pieces whereof the surfaces are planar or the roughness is low in relation to the wavelength of the ultrasounds. Under those conditions, the acoustic coupling is ensured and the energy transmitted into such pieces is sufficient to perform the monitoring.

However, the performance of these techniques, which use one or multiple standard elements, is quickly limited when complex geometries or surfaces are monitored. Different paths are currently being explored to resolve this problem.

One known solution consists of processing the signals, when they are transmitted or received, using very complex mathematical algorithms. Such methods use transducers placed in contact with objects to be monitored or away from said objects. These methods are therefore difficult to implement and are fairly quickly limited because the signals are greatly disrupted by the complex interface between a transducer and an object to be monitored or by the need to precisely know the parameters of the acquisition, such as the geometric parameters.

The acoustic coupling can be optimized by connecting a transducer to a device that ensures a local immersion (first solution) or a flexible silicone wedge (second solution).

The first solution can be very difficult to implement, or even impossible to use, since it requires locally sealing a feed line. The second solution, although it optimizes the acoustic coupling, does not offset the aberrations undergone by the ultrasonic beam passing through the interface between the wedge and the piece to be monitored.

Flexible transducers also exist that offset, to a certain extent, the geometric variations to optimize the acoustic coupling and that integrate a profilometer. Said profilometer makes it possible to offset, using delay laws, the aberrations that the ultrasonic beam may undergo when it passes through a complex interface.

In this respect, we can cite flexible contact transducers, such as SFT transducers, i.e. smart flexible transducers, and conformable transducers. The operation of such transducers is explained in the following documents to which one will refer:

[1] WO 00/33292, "TRANSDUCTEUR ULTRASONORE DE CONTACT, A ELEMENTS MULTIPLES", ("MULTIELEMENT ULTRASONIC CONTACT TRANSDUCER"), corresponding to U.S. Pat. No. 6,424,597,

[2] WO 2005/050617, "TRANSDUCTEUR ULTRASONORE DE CONTACT, A MULTIPLES ELEMENTS EMETTEURS ET MOYENS DE PLAQUAGE DE CES ELEMENTS", ("ULTRASONIC CONTACT TRANSDUCER COMPRISING MULTIPLE EMITTING ELEMENTS AND MEANS FOR PRESSING SAID ELEMENTS"), corresponding to US 2007/0167800.

However, a transducer of this type is put directly in contact with a piece to be monitored, which leads to the existence of a dead zone of several millimeters under the surface of the piece, in which zone no monitoring can be done.

To resolve this problem, it is known to connect a delay line to each element of the "SFT" or "conformable" transducer, but this is done to the detriment of that transducer's flexibility.

Furthermore, the proximity of the elements comprised by that transducer is a parameter that cannot be separated from the sensitivity thereof. Indeed, to ensure the flexibility of the transducer, the elements are separated by ball pivots or by a soft body that harms the transducer's performance and these features make it a specific transducer.

Lastly, the technological limits for realizing elements reduce the directivity of such transducers and do not make it possible to perform monitoring with large incline angles of the ultrasonic beam.

DESCRIPTION OF THE INVENTION

The present invention aims to resolve the aforementioned drawbacks.

In the invention, a standard rigid phased array transducer is provided with a wedge whereof at least the front face is flexible. The acoustic coupling between the set of elements and an object to be monitored is ensured by the wedge, the deformable front face of which is capable of fitting the shape of a complex surface.

Moreover, according to another feature of the invention, real-time information on the local deformation of said front face is used to offset the delay laws during focusing of the ultrasound waves.

Of course, techniques exist that use a phased array transducer, mounted on a flexible wedge without instrumentation, and in which the surface of the object to be monitored is known a priori. Parameters such as the delay laws are then applied as a function of the position of the transducer.

These techniques are interesting in the case of a slightly irregular surface, but their interest becomes very limited when the surface is warped, due to positioning errors of the transducer regarding its altitude, incline and placement, and lack of knowledge of the surface's profile. To resolve this, heavy calibration procedures are then carried out.

The present invention is simpler to implement; it uses a traditional phased array transducer, which is mounted on a wedge whereof the front face is flexible and that is equipped with a profilometer. This profilometer allows electronic control means to calculate the deformation of the front face and the adapted delay laws.

The real-time application of these delay laws by the electronic control means makes it possible to offset the surface variations during the formation of the ultrasonic beam and to maintain optimized characteristics for the latter in the monitored object.

To take complex geometries into account, flexible contact phased array ultrasound transducers also exist. These transducers enable good acoustic coupling and are provided with instrumentation (see documents [1] and [2]).

But the performance of these transducers is limited when it involves focusing ultrasonic waves with strong inclines; moreover, these transducers lead to a significant dead zone under the surface of the monitored object.

The present invention uses the refraction of ultrasonic waves, which is the best way to focus said waves with strong inclines, under the surface of the monitored object. Moreover, the wedge plays the role of delay line and makes it possible to reduce the dead zone, or listening zone, under said surface.

Furthermore, the known techniques use either a flexible wedge without instrumentation, or a flexible phased array transducer, coupled to a profilometer.

The relevance of the present invention lies in the maintenance of an optimized coupling with the object using a wedge, whereof at least the front face is flexible, and a profilometer integrated in the transducer.

This profilometer makes it possible to provide the geometry variations to a processor in which an algorithm is implemented to calculate adapted delay laws.

Specifically, the present invention concerns a phased array ultrasound transducer, said transducer comprising:

a set of elements that are rigidly integral with each other, at least part of the elements serving as ultrasound transmitters, and a wedge having a front face, designed to be in contact with the surface of an object to be monitored, and a rear face that is opposite the front face and with which the set of elements is made integral, this transducer being characterized in that at least the front face of the wedge is flexible to be able to be applied against the surface of the object, and in that the transducer also comprises a profilometer to measure variations of the object's surface and supply signals representative of those variations, in order to allow the ultrasound transmitters to create a focused ultrasonic beam, the characteristics of which are controlled relative to the object.

Preferably, the entire wedge is flexible.

According to one preferred embodiment of the transducer of the invention, the wedge comprises a deformable jacket and a fluid that is contained in the deformable jacket.

Preferably, the transducer according to the invention also comprises a rigid portion with which the profilometer is made rigidly integral.

According to one preferred embodiment of the invention, the profilometer comprises:

mechanical elements, each mechanical element comprising a portion that is mobile in relation to the rigid portion of the transducer and comprises first and second ends, the first end of the mobile portion being capable of pressing the front face of the wedge against the surface of the object, and measuring means to measure the distance of the second end of each of the mobile portions in relation to the rigid portion of the transducer, these measuring means being capable of providing signals representative of the distances thus measured.

According to one specific embodiment, the mechanical elements form two parallel rows on either side of the wedge.

According to one preferred embodiment of the device according to the invention, the rigid portion of the transducer includes parallel holes, in which the mobile portions are respectively capable of sliding, and each mechanical element also comprises elastic means that are capable of separating the first end of the mobile portion corresponding to that mechanical element from the rigid portion.

According to one specific embodiment of the invention, the measuring means are capable of optically measuring the distance of the second end of the mobile portion of each mechanical element in relation to a zone of the rigid portion and comprise:

light transmitting means, fastened to the rigid portion and capable of transmitting light toward the second end, this second end being capable of reflecting said light, and light receiving means, fastened to the rigid portion and capable of receiving the light thus reflected, these light receiving means being capable of providing signals representative of the distance of said second end in relation to the corresponding zone.

Preferably, the transducer according to the invention also comprises control means, capable of:

creating excitation pulses of the ultrasound transmitters, establishing, from the signals supplied by the profilometer, delay laws allowing the ultrasound transmitters to create the focused ultrasonic beam, and applying these delay laws to the excitation pulses so as to create the focused ultrasonic beam.

According to a first specific embodiment of the invention, the rest of the elements of the set of elements rigidly integral with each other serve as ultrasound receivers, designed to supply signals allowing the formation of images relating to the object.

According to a second specific embodiment of the invention, all of the elements of the set of elements rigidly integral with each other serve both as ultrasound transmitters and receivers, the ultrasound receivers being designed to supply signals allowing the formation of images relating to the object.

The invention is applicable to any two- or three-dimensional monitoring requiring offsetting of the delay laws to correct a surface aberration.

Regarding two-dimensional geometries, the invention for example makes it possible to monitor feed lines with large dimensions, in particular weld seams that are present thereon.

Regarding three-dimensional geometries, the invention for example makes it possible to monitor tappings, elbows, and, more generally, any part having a three-dimensional geometry.

In the medical field, the invention applies in particular to diagnostic ultrasounds of the calcaneum (heel bone), skull and breasts.

BRIEF DESCRIPTION OF THE DRAWINGS

The present invention will be better understood upon reading the description of embodiments provided below, purely for information and in no way limitingly, in reference to the appended drawings, in which.

DETAILED DESCRIPTION OF SPECIFIC EMBODIMENTS

Figure 1:
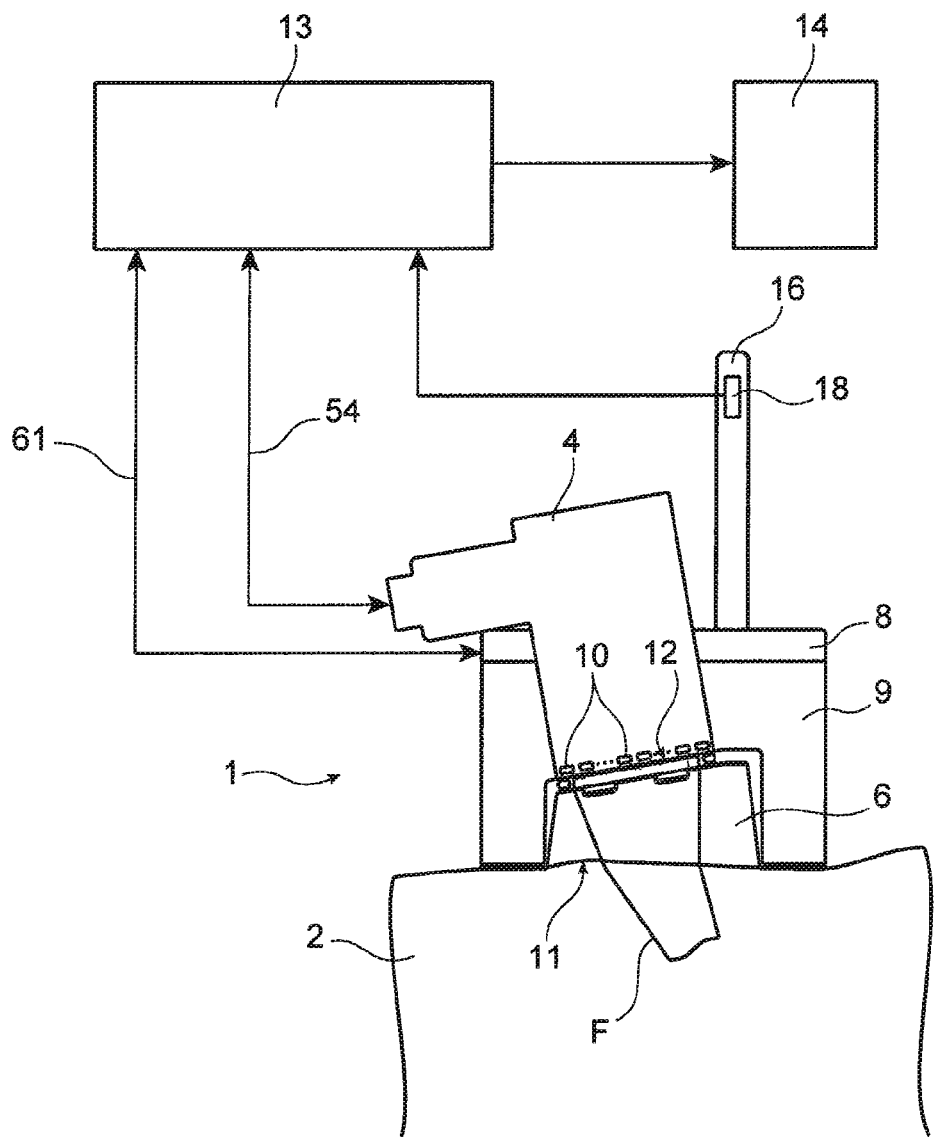
FIG. 1 diagrammatically illustrates the principle of the invention.

The ultrasound transducer 1 according to the invention, which is diagrammatically illustrated in FIG. 1, is designed to monitor an object 2 and essentially comprises a traditional rigid ultrasound transducer 4, a wedge 6 and a profilometer 8.

The traditional transducer 4 comprises a set of piezoelectric elements 10 that are rigidly integral with each other and serve as both ultrasound transmitters and receivers.

The front face 11 of the wedge 6 is designed to be in contact with the surface of the object to be monitored 2 and its rear face 12, opposite its front face, is fixed to the traditional transducer 4 and is in contact therewith. Moreover, at least the front face of the wedge 6 is flexible to be able to be applied against the surface of the object 2 but, in the example, the entire wedge 6 is flexible to simplify the design of the transducer 1 according to the invention.

The profilometer 8 is designed to measure surface variations of the object 2 and to supply electrical signals representative of those variations, in order to allow the ultrasound transmitters to create, in the object 2, a focused ultrasonic beam F whereof the characteristics are controlled in relation to the object.

It is specified that the traditional ultrasound transducer 4 and the profilometer 8 are made rigidly integral with a portion 9 of the transducer 1 according to the invention. This portion 9 is rigid and constitutes the body of the transducer 1.

In the example of FIG. 1, the transducer 1 according to the invention is provided with control means 13 that are electrically connected to the traditional transducer 4 and to the profilometer 8 and are capable of:

creating electrical excitation pulses of the elements 10 so that said elements emit ultrasounds, establishing, from the signals supplied by the profilometer 8 and using a suitable calculation algorithm, delay laws allowing the elements 10 to create the focused ultrasonic beam F, and applying these delay laws to the excitation pulses so as to create the focused ultrasonic beam F.

Furthermore, in the example of FIG. 1, the control means 13 are capable of processing the electrical signals they receive from the piezoelectric elements, the latter elements then serving as ultrasound receivers, in order to form images relating to the object. These images are displayed on a video monitor 14.

Moreover, in the example of FIG. 1, the transducer 1 according to the invention is fastened to an articulated mechanical arm 16. This articulated arm makes it possible to obtain the position and orientation of the transducer in the fixed reference of the object to be controlled 2. Sensors 18, with which the arm 16 is provided, make it possible to situate said transducer in space and measure its orientation during its movement in relation to the object 2, as indicated in documents [1] and [2] to which one will refer.

The position and orientation supplied by the sensors 18 are used by the control means 13 to determine the positions of the transducer in relation to the object 2.

Figure 2:
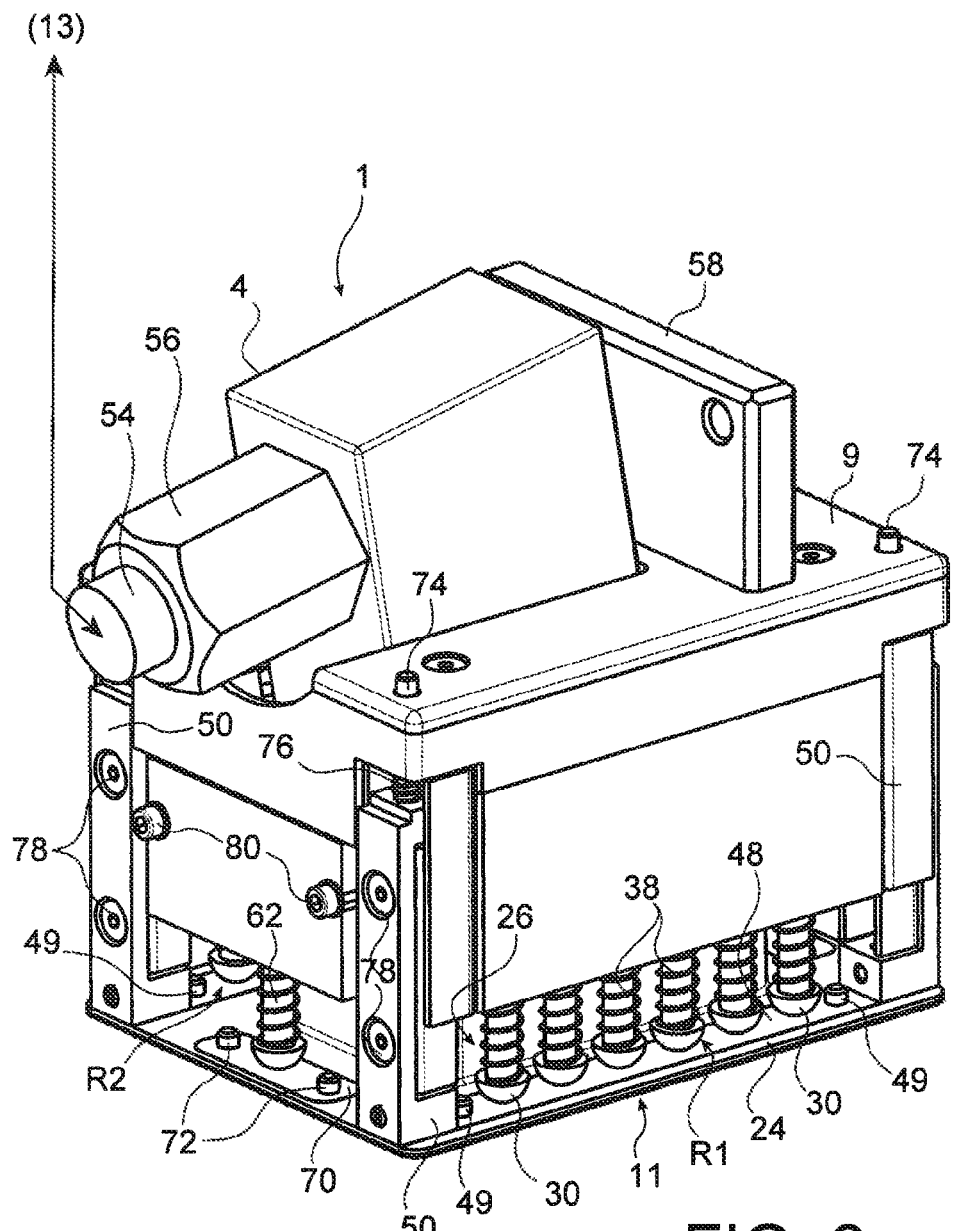
FIG. 2 is a diagrammatic perspective view of a specific embodiment of the transducer according to the invention.
Figure 3:
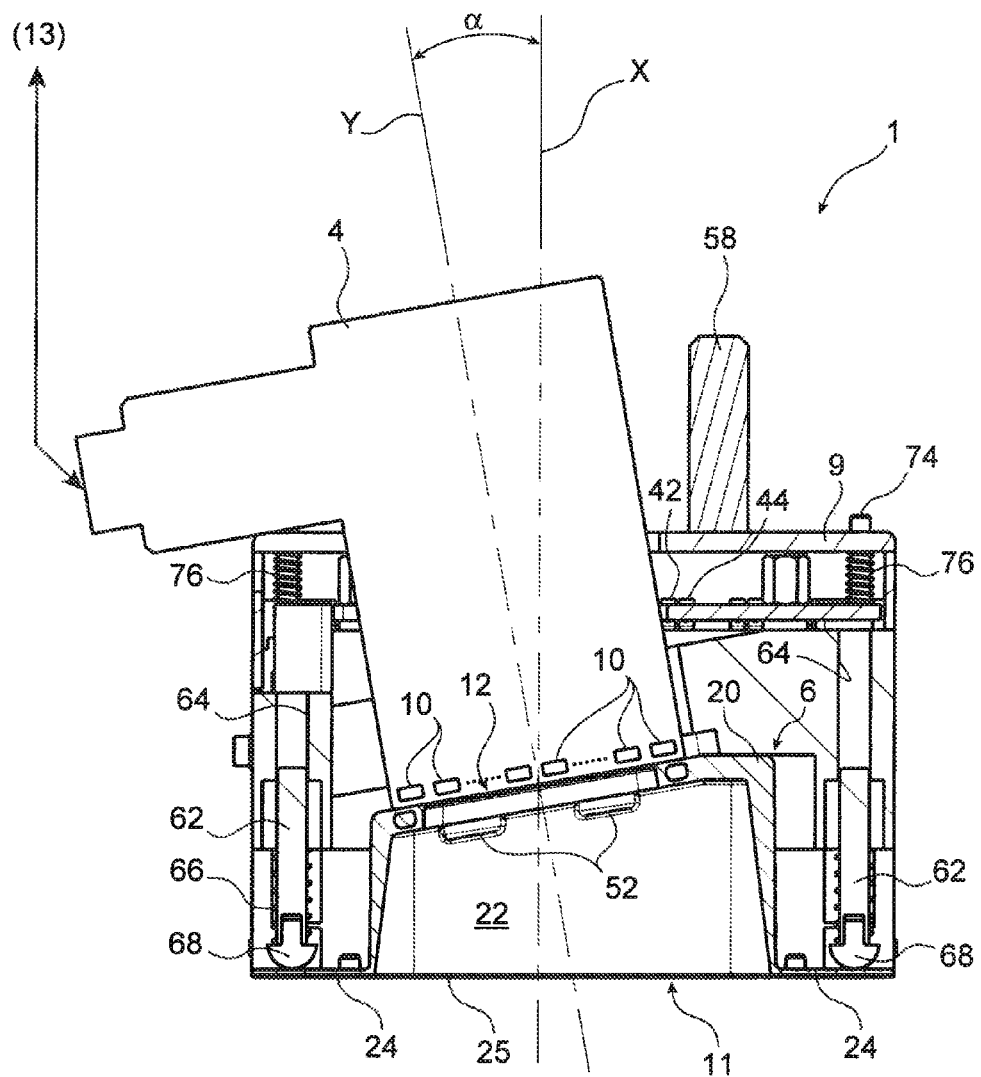
FIG. 3 is a diagrammatic cross-sectional view of the transducer of FIG. 1, showing the flexible wedge and the ultrasound transmitters-receivers of said transducer.
Figure 4:
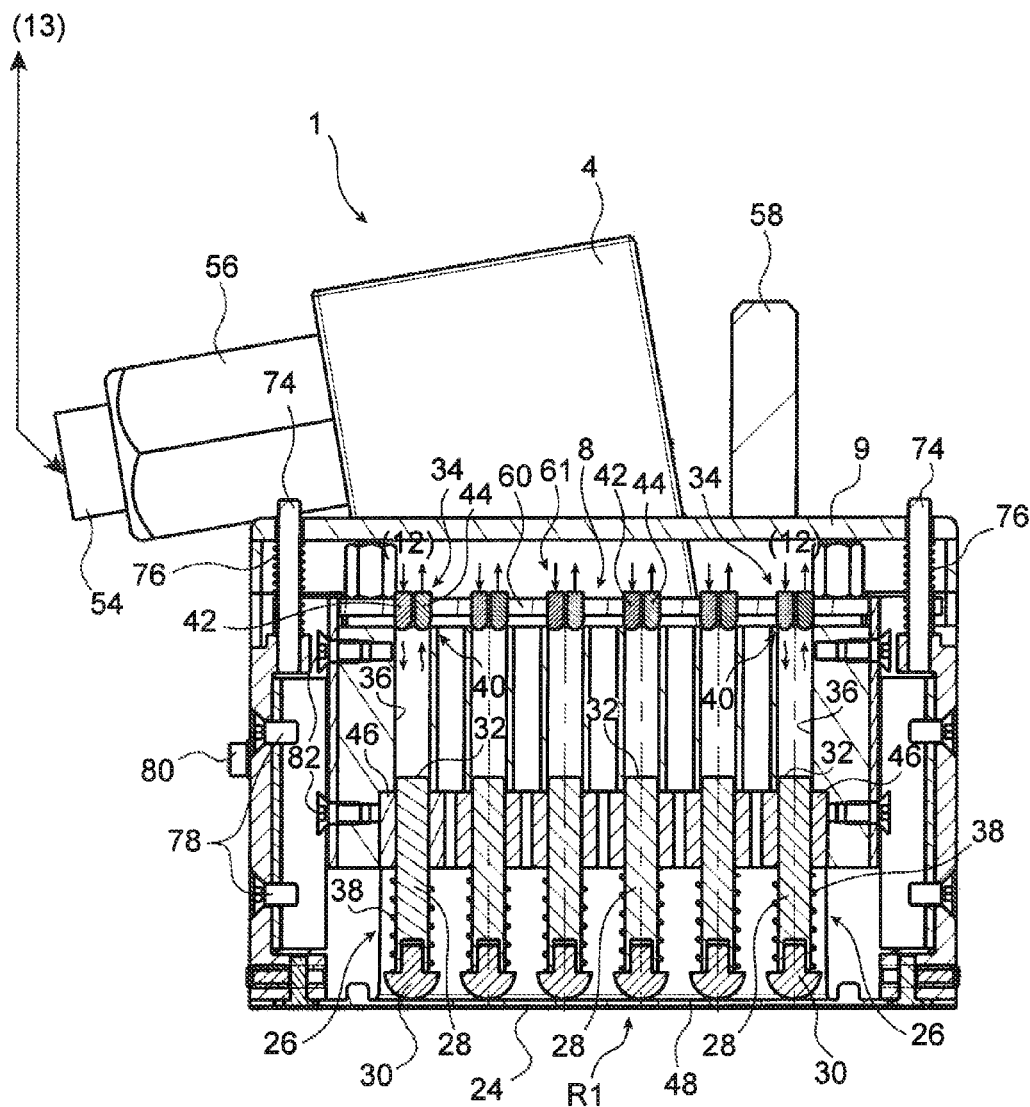
FIG. 4 is another diagrammatic cross-sectional view of the transducer of FIG. 1, showing the profilometer of said transducer.

FIGS. 2 to 4 diagrammatically show, in more detail than in FIG. 1, the transducer 1 according to the invention.

FIG. 2 is a perspective view of this transducer 1 that shows a plane of symmetry; FIG. 3 is a cross-sectional view along said plane of symmetry which cuts the wedge 6; and FIG. 4 is another cross-sectional view along another plane that is parallel to the plane of symmetry and cuts a row of moving elements comprised by the profilometer 8.

In FIG. 3, we therefore see the wedge 6. Said wedge comprises a deformable jacket 20 and a fluid 22 that is contained in the deformable jacket. The jacket also includes a lateral extension 24 at the front face 11 of the wedge, which makes it substantially hat-shaped. The jacket 20 is also closed, at its base (on the front face 11 side), by a deformable sheet 25.

The profilometer 8 comprises (FIG. 4):

mechanical elements 26, each mechanical element comprising a portion 28 that is mobile in relation to the body 9 of the transducer 1 and comprises first and second ends 30 and 32, the first end 30 of the moving portion 28 being capable of pressing the front face 11 of the wedge 6 against the surface of the object 2 (FIG. 1), and measuring means 34 to measure the distance of the second end 32 of each of the moving portions 28 in relation to the body 9 of the transducer 1, this measuring means 34 being capable of supplying signals representative of the distances thus measured.

In the illustrated example, the mechanical elements 26 form two parallel rows R1 and R2 (FIG. 2) on either side of the wedge 6. The row R1 is shown in more detail in FIG. 4. This configuration is in no way limiting; there could thus be only one row R1, on one side of the wedge 6 or on the other side.

The body 9 of the transducer 1 includes parallel holes 36, in which the moving portions 28, or pistons, are respectively capable of sliding, and each mechanical element 26 also comprises elastic means 38, springs in the example, which are capable of separating the first end 30 of the piston 28 corresponding to said mechanical element 26 from the body 9.

The measuring means 34 are capable of optically measuring the distance of the second end 32 of the piston of each mechanical element 26 in relation to a zone 40 of the body 9 and comprise:

light transmitting means 42, fastened to the body 9 and capable of transmitting light toward the second end 32, said second end being capable of reflecting said light, and light receiving means 44, fastened to the body 9 and capable of receiving the light thus reflected, this light receiving means 44 being capable of supplying signals representative of the distance of said second end 32 in relation to the corresponding zone 40.

We will now go over the different components of the transducer 1 in more detail.

The deformation of the flexible portion, i.e. the wedge 6, of the transducer 1 is for example 5 mm for a bearing force of 10 to 20 newtons. This flexible portion is maintained by the traditional transducer 4, which is itself rigidly integral with the body 9. The latter defines the geographical reference of the transducer 1 in the reference of the object 2 to be monitored.

The body 9 is fastened to the arm 16 (FIG. 1), which is provided with engines (not shown) to allow the movement of the transducer 1 in order to monitor the various zones of the object 2 (FIG. 1). In another embodiment, the movement of the transducer 1 is manual and is made possible using an encoder and an inclinometer (not shown).

Linear ball bearings 46 are also housed in the body 9, as shown in FIG. 4—see also document [2]. In these linear ball bearings 46, the pistons 28, the diameter of which is for example 3 mm, move.

The ends 30 of the pistons are hemispherical in shape (diameter 5 mm for example) and are in contact with foils 48 (FIG. 2) to better move. These foils are metal sheets that are fixed using clips 49 on the rims (lateral extension 24) of the flexible wedge 6, as shown in FIG. 2, and are present to give the rims transverse resistance. These rims of the flexible wedge 6 are also held by four guide rails 50 that are made integral with the body 9, as shown in FIG. 2.

In agreement with the authorized deformations, the travel of the pistons 28 goes, in the example, from 5 mm to 8 mm.

The body 9 is designed to facilitate the installation of the traditional transducer 4 and its fastening on inserts 52, or nuts, that are cast in the wedge 6, as shown in FIG. 3, taking into account the bulk of the traditional transducer 4 and a strand of coaxial cables 54 by which this transducer 4 is electrically connected to the control means 13 (FIG. 1). The traditional transducer 4 is provided with screws (not shown) that one screws into the inserts (from the outside of the wedge). Only two of the four inserts used are visible in FIG. 3.

In FIG. 3, references X and Y show a normal direction to the front face 11 of the wedge 6 and a normal direction to the rear face 12 of said wedge, respectively. In the example, the angle α between the directions X and Y is 10°.

In FIGS. 2 and 4, reference 56 designates a gland that is connected to the strand of cables 54 and reference 58 designates a member that is made rigidly integral with the body 9 and makes it possible to fix said body to the arm 16 (FIG. 1).

Fastened to the body 9 is an optoelectronic card 60, or measuring circuit, that supports the measuring means 34 and therefore serves to measure the respective piston heights. The card 60 integrates a pair of transmission-reception means 42, 44 per piston 28. In the example, the transmission means 42 are light-emitting diodes and the receiving means are photodetectors 44.

Each light-emitting diode emits light toward the end 32 of the corresponding piston, that end reflects it and the corresponding photodetector 44 detects the reflected light. The measurement of the separation from the piston head (end 32) is done using the light reflected by the piston head and the current created by the corresponding photodetector.

The specifications of the card 60 are identical to those of the light transmitting-receiving means included by the ultrasonic contact transducer described in document [2] to which one will refer. A cable 61 connects said card 60 to the control means 12 (FIG. 1) and integrates all of the electrical connections of the light-emitting diodes and the photodetectors with these control means 12.

The measuring points are therefore located in the reference of the transducer 1 in specific locations (zones 40) that are defined by the positions of the pistons 28. The voltages supplied by the photodetectors 44 are measured for specific altitudes of the piston heads in order to create a conversion table.

During a measurement and using this conversion table, or calibration table, the voltages are converted into millimeters.

The coordinates of the measurement points are representative of the surface of the object to be monitored and will then be used by an algorithm that reconstructs said surface using an interpolation function. A second function makes it possible to recalculate the coordinates of the elements 10 of the traditional transducer 4 in relation to the surface of the object, said surface being reconstructed in the reference of the object or the traditional transducer 4.

Another algorithm makes it possible to calculate the acoustic paths separating the elements 10 from the focal point of the ultrasonic beam F (FIG. 1).

These paths are then converted into time of flight, then delays. These delays make it possible to obtain optimized delay laws to offset the surface variations of the monitored object. These same laws are then used by the control means 13 to individually control the elements 10.

The base of the wedge 6 includes a fine sheet of silicone that makes up the lateral extension 24 mentioned above. As seen in FIGS. 2, 3 and 4, the pistons 28 bear on this sheet and thereby ensure the acoustic coupling through relaxation of the springs 38.

The deformable sheet 25 is for example also made of silicone and is for example stuck on the lateral extension 24.

As seen above, the pistons 28 associated with the springs 38 slide in the body 9, which also serves as altitude reference for the measuring card 60; on this card are the pairs of light-emitting diodes 42 and photodetectors 44 that are situated above each piston 28 and the function of which are to emit a light wave toward the head 32 of each piston and to convert the optical intensity reflected by said head into voltage, respectively; these voltages are then converted into altitudes to reconstruct the surface of the monitored object.

FIGS. 2 and 3 show that the body 9 is provided with two other pistons 62 that are placed on either side of the wedge 6, between the rows of pistons R1 and R2, to stick the lateral extension 24 of the wedge against the object to be monitored. These pistons 62 slide in holes 64 provided in the body 9. Springs 66 are provided to push the hemispherical heads 68 of the pistons 62 toward the lateral extension 24, as shown.

Rectangular foils 70 are again fastened to this lateral extension 24 using clips 72 and the pistons 62 bear on the lateral extension 24 via foils 70, as shown. In FIGS. 2 to 4, the axes 74 serve to guide the regulator springs 76.

The screws 78, 80, 82 of FIGS. 2 and 4 serve to fasten various elements of the body 9 to each other.

In one embodiment of the invention, one can use inertial sensors to obtain the position and orientation of the transducer 1, as mentioned in document [2].

It is also specified that the light-emitting diodes 42 can be controlled so as to emit continuous light beams or, on the contrary, broken ones, in particular light pulses.

Moreover, in one embodiment of the transducer 1, instead of using the light transmitters-receivers 42-44, optical fibers are supplied by a single light source, or by several light sources at a rate of one source per fiber, and are used to transmit the light toward the two respective ends 32 of the moving portions 28, and other optical fibers are used to transmit the lights respectively reflected by these second ends to photodetectors. The source(s) and the photodetectors can be placed in the control means 13, where the photocurrents generated by the photodetectors when the latter receive reflected light are processed (see document [2]).

In the examples of the invention just described, the remote measuring means, making it possible to detect movements of the pistons, are optical means, therefore allowing optical detection of said movements.

However, these optical means can be replaced by magnetic means.

In an example that is not illustrated, each diode 42-photodetector 44 assembly of FIG. 3 is replaced by a Hall effect sensor and a magnet is fastened on the end 32 of the moving potion of the corresponding piston. The Hall effect sensor is thus capable of supplying a signal that is a function of the distance between said sensor and said magnet. By using suitable means for controlling the sensor and processing the signals supplied by it, it is also possible to measure the desired distance (see also document [2]).

Moreover, the examples of the invention that were provided use both ultrasound transmitting and receiving elements. A person skilled in the art can adapt these examples in case of transducers comprising elements provided only to emit ultrasounds and other elements provided only to receive ultrasounds.

Moreover, in the invention, one can use a transducer comprising a linear strip of ultrasonic elements 10, but the invention is not limited to such a transducer. As in documents [1] and [2], one can use a matrix transducer, comprising a matrix of ultrasonic elements 10.

The invention claimed is:

1. A phased array ultrasonic contact transducer, said transducer comprising:
   a set of elements that are rigidly integral with each other, at least part of the elements serving as ultrasound transmitters, and
   a wedge having a front face, designed to be in contact with the surface of an object to be monitored, and a rear face that is opposite the front face and with which the set of elements is made integral,
   this transducer being characterized in that at least the front face of the wedge is flexible to be able to be applied against the surface of the object, and in that the transducer also comprises a profilometer to measure variations of the object's surface and supply signals representative of those variations, in order to allow the ultrasound transmitters to create a focused ultrasonic beam, the characteristics of which are controlled relative to the object, the transducer further comprises a rigid portion with which the profilometer is made rigidly integral, wherein the profilometer includes:
   mechanical elements, each mechanical element comprising a portion that is mobile in relation to the rigid portion of the transducer and comprises first and second ends, the first end of the mobile portion being capable of pressing the front face of the wedge against the surface of the object, and
   measuring means to measure the distance of the second end of each of the mobile portions in relation to the rigid portion of the transducer, these measuring means being capable of providing signals representative of the distances thus measured.

2. The transducer according to claim 1, wherein the entire wedge is flexible.

3. The transducer according to claim 2, wherein the wedge comprises a deformable jacket and a fluid that is contained in the deformable jacket.

4. The transducer according to claim 1, wherein the mechanical elements form two parallel rows on either side of the wedge.

5. The transducer according to claim 1, wherein the rigid portion of the transducer includes parallel holes, in which the mobile portions are respectively capable of sliding, and each mechanical element also comprises elastic means that are capable of separating the first end of the mobile portion corresponding to that mechanical element from the rigid portion.

6. The transducer according to claim 1, wherein the measuring means are capable of optically measuring the distance of the second end of the mobile portion of each mechanical element in relation to a zone of the rigid portion and comprise:
   light transmitting means, fastened to the rigid portion and capable of transmitting light toward the second end, this second end being capable of reflecting said light, and
   light receiving means, fastened to the rigid portion and capable of receiving the light thus reflected, these light receiving means being capable of providing signals representative of the distance of said second end in relation to the corresponding zone.

7. The transducer according to claim 1, also comprising control means, capable of:
   creating excitation pulses of the ultrasound transmitters,
   establishing, from the signals supplied by the profilometer, delay laws allowing the ultrasound transmitters to create the focused ultrasonic beam, and
   applying these delay laws to the excitation pulses so as to create the focused ultrasonic beam.

8. The transducer according to claim 1, wherein the rest of the elements of the set of elements rigidly integral with each other serve as ultrasound receivers, designed to supply signals allowing the formation of images relating to the object.

9. The transducer according to claim 1, wherein all of the elements of the set of elements rigidly integral with each other serve both as ultrasound transmitters and receivers, the ultrasound receivers being designed to supply signals allowing the formation of images relating to the object.

* * * * *